United States Patent [19]

Fenton, Jr.

[11] Patent Number: 4,627,835
[45] Date of Patent: Dec. 9, 1986

[54] TUBING ASSEMBLY FOR INFUSION DEVICE

[75] Inventor: Paul V. Fenton, Jr., Marblehead, Mass.

[73] Assignee: Strato Medical Corporation, Beverly, Mass.

[21] Appl. No.: 710,011

[22] Filed: Mar. 11, 1985

[51] Int. Cl.4 .................................................. A61M 5/00
[52] U.S. Cl. ..................................... 604/67; 604/154; 604/218; 128/DIG. 1
[58] Field of Search ................................ 604/151–155, 604/218, 280, 65, 67, 131, 135; 128/DIG. 12, DIG. 13, DIG. 1

[56] References Cited

U.S. PATENT DOCUMENTS

| | | | |
|---|---|---|---|
| 3,279,653 | 10/1966 | Pfleger | 604/135 |
| 3,886,938 | 6/1975 | Szabo et al. | 604/135 |
| 4,085,747 | 4/1978 | Lee | 128/DIG. 12 |
| 4,132,231 | 1/1979 | Puccio | 604/131 |
| 4,136,802 | 1/1979 | Mascia et al. | 222/340 |
| 4,202,333 | 5/1980 | Thill et al. | 128/218 A |
| 4,228,922 | 10/1980 | Takeshita | 604/135 |
| 4,298,000 | 11/1981 | Thill et al. | 604/135 |
| 4,333,459 | 6/1982 | Becker | 604/135 |
| 4,381,006 | 4/1983 | Genese | 604/135 |
| 4,424,720 | 1/1984 | Bucchianeri | 604/155 X |
| 4,430,079 | 2/1984 | Thill et al. | 604/154 |
| 4,437,859 | 3/1984 | Whitehouse et al. | 604/131 |
| 4,470,317 | 9/1984 | Sabloewski et al. | 604/135 |

Primary Examiner—Stephen C. Pellegrino
Attorney, Agent, or Firm—Lahive & Cockfield

[57] ABSTRACT

An infusion device for a syringe includes a ratcheted stepper motor driven intermittently under the control of a control circuit to advance a syringe plunger driver. Different speeds are determined by the detected size of the syringe in the device. A clutch assembly disengageably connects the plunger driver to a drive belt driven by the stepper motor.

A connector for a tubing set has a syringe-connect portion located in a recess of the connector, and cooperates with a force sensor in the device to detect occlusions. The connector has annular projecting portions with parallel, spaced apart actuating surfaces for engagement of the force sensor in either of two positions of the connector in the device. The connector is adapted to indicate to a sensor in which position it is located.

12 Claims, 15 Drawing Figures

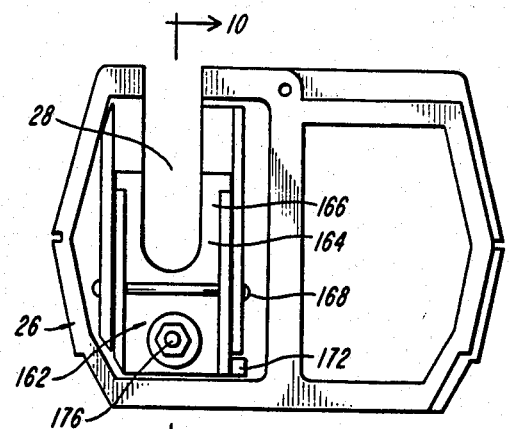
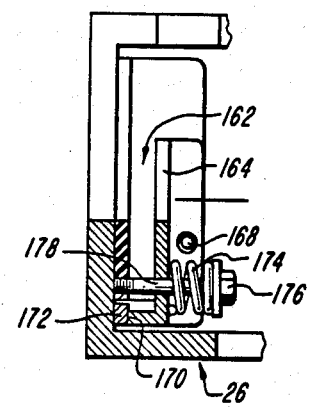
FIG. 9    FIG. 10
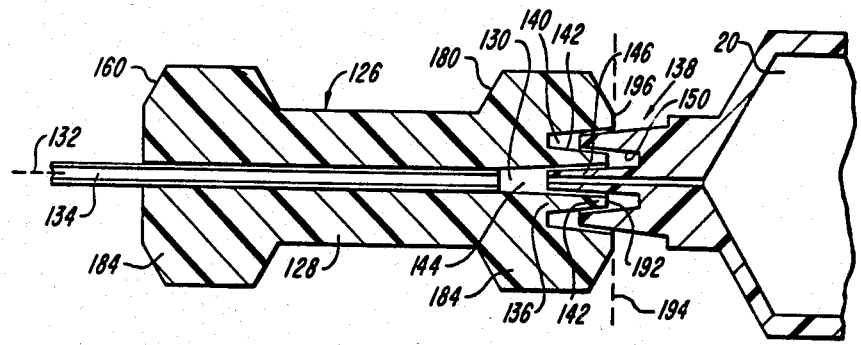
FIG. 12
FIG. 13
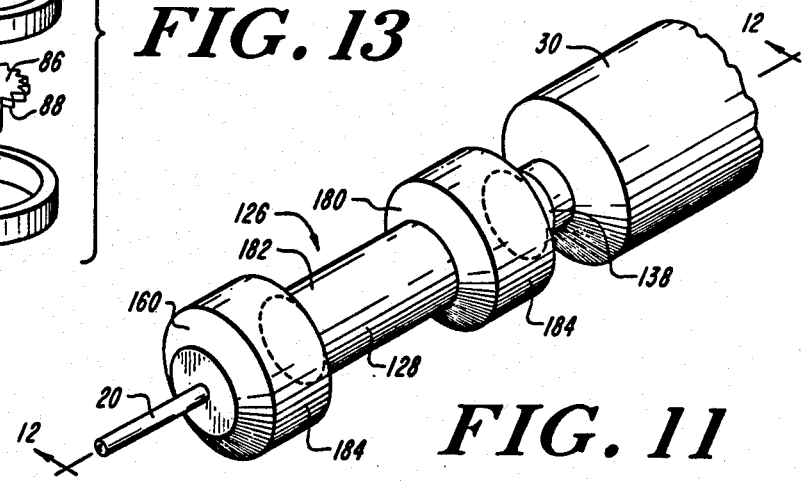
FIG. 11

TUBING ASSEMBLY FOR INFUSION DEVICE

BACKGROUND OF THE DISCLOSURE

This invention relates to devices for driving a fluid-dispensing syringe and, more particularly, to motor driven devices used in conjunction with tubing sets having specially configured connectors.

An infusion device is generally used to control the automatic dispensing of fluids from a syringe, for example, to a capillary tube which in turn might introduce those fluids to a patient. In many cases, it is extremely important that the rate of fluid delivery be correctly selected and accurately controlled.

In the prior art, several types of infusion devices have been used. One type of device incorporates a housing for supporting a syringe and utilizes an electrical motor, and associated drive circuitry configured to drive the plunger of the syringe at a constant rate. Typically such a configuration incorporates a lead screw coupling between the electric motor and the plunger. Alternatively, direct gear couplers have been used. Stepper motors have also been used, but the power requirements for stepper motors have been greater than is desirable for a light, compact device.

In infusion device U.S. patent application Ser. No. 676,728, assigned to the same assignee as the present application, a spring-driven infusion device is shown in which two or more substantially constant spring forces can be selectively engaged to drive different capacity syringes.

It is also desirable to provide infusion devices that can accomodate different size syringes and that can provide different drive rates for the respective syringes in an automatic manner that is not dependent on operator selection. It is furthermore desirable to provide tubing sets for infusion devices that make the use of the devices more convenient. It is an object of the present invention to provide an improved infusion device with these characteristics.

Another object is to provide such an infusion device that operates automatically and reliably without excessive controls or control devices, that accommodates different size syringes, and that varies the drive rate for the syringe plunger according to the size of the syringe.

It is still another object to provide such an infusion device with improved means for detecting occlusion and emptying of the syringe.

Another object is to provide an infusion device that will cooperate with a specially configured tubing set connector for control of the operation of the infusion device.

Still another object is to provide a tubing set connector for rapid and reliable and sterile connection to an infusion device. Another object is to provide such a connector that will cooperate with an infusion device in determining the position of syringes in the infusion device and in controlling the speed of operation of a syringe plunger in the device accordingly.

SUMMARY OF INVENTION

The invention comprises a tube assembly for use with a syringe and an infusion device adapted for supporting the syringe and driving the plunger of the syringe along a reference axis toward a fluid dispensing outlet port thereof, wherein the infusion device includes a support member for supporting the tube assembly, comprising an elongated flexible tube defining a central bore therethrough, and a rigid connector member affixed to the tube and including means for coupling the input port to the outlet port of the syringe, and defining a linear central bore extending therethrough, the bores defining a continuous passageway, extending from an input port of the connector member, and the connector member, wherein the connector member includes at least two support portions spaced apart along the axis of the connector member central bore and an interface portion connecting the support portions, and wherein the outer surfaces of the support portions are substantially identical in shape, the shape being adapted to interfit with the support member, whereby either of the support portions may be supported by the support member.

Preferably the outer surfaces of the support portions are surfaces of revolution.

In one embodiment a tube assembly like that described is used with an infusion device that further includes a sensor for sensing force applied thereto in the direction of said reference axis, and the connector member includes at least two actuating means for selective interfering engagement with the sensor. The actuating means may include at least two parallel actuating surfaces for abutting engagement with the sensor, wherein the actuating surfaces are spaced apart along the axis of the connector member central bore, and wherein the actuating surfaces are annular surfaces, where each of the annular surfaces is defined by an associated one of the support portions.

Also, the tube assembly, for use with a syringe and infusion device, wherein the device further includes a sensor for sensing the position of the outlet port of the syringe, may include a connector member having surface regions adapted for sensing by the sensor, each of the regions being representative of an associated one of the support portions being supported by the support member. The sensor may be an optical sensor, and the regions characterized by differing optical reflectivity, or a mechanically actuated switch, and the regions characterized by different physical geometry, or a conductivity sensor, and the regions characterized by different electrical conductivity.

The tube assembly furthermore may have the input port coupling means inset within the connector member.

BRIEF DESCRIPTION OF THE DRAWINGS

The foregoing and other objects of this invention, the various features thereof, as well as the invention itself may be more fully understood from the following description, when read together with the accompanying drawings in which:

FIG. 9 is a sectional view of the inside front of the device along the line 9—9 of FIG. 3;

FIG. 10 is a sectional view of the front of the device along the line 10—10 of FIG. 9;

FIG. 11 is a perspective view of the connector;

FIG. 12 is a sectional view of the connector;

FIG. 13 is an exploded view of the ratchet assembly for the stepper motor of the infusion device;

DESCRIPTION OF THE PREFERRED EMBODIMENT

Figure 1:
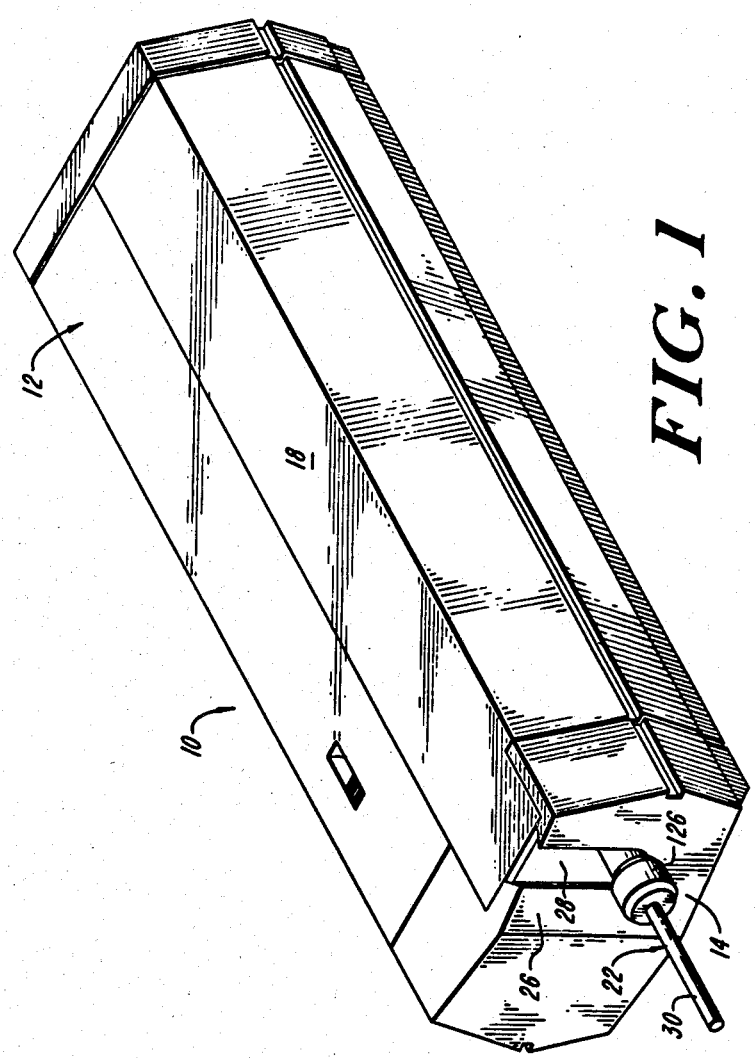
FIG. 1 shows a perspective view of an exemplary embodiment of an infusion device in accordance with the invention.
Figure 2:
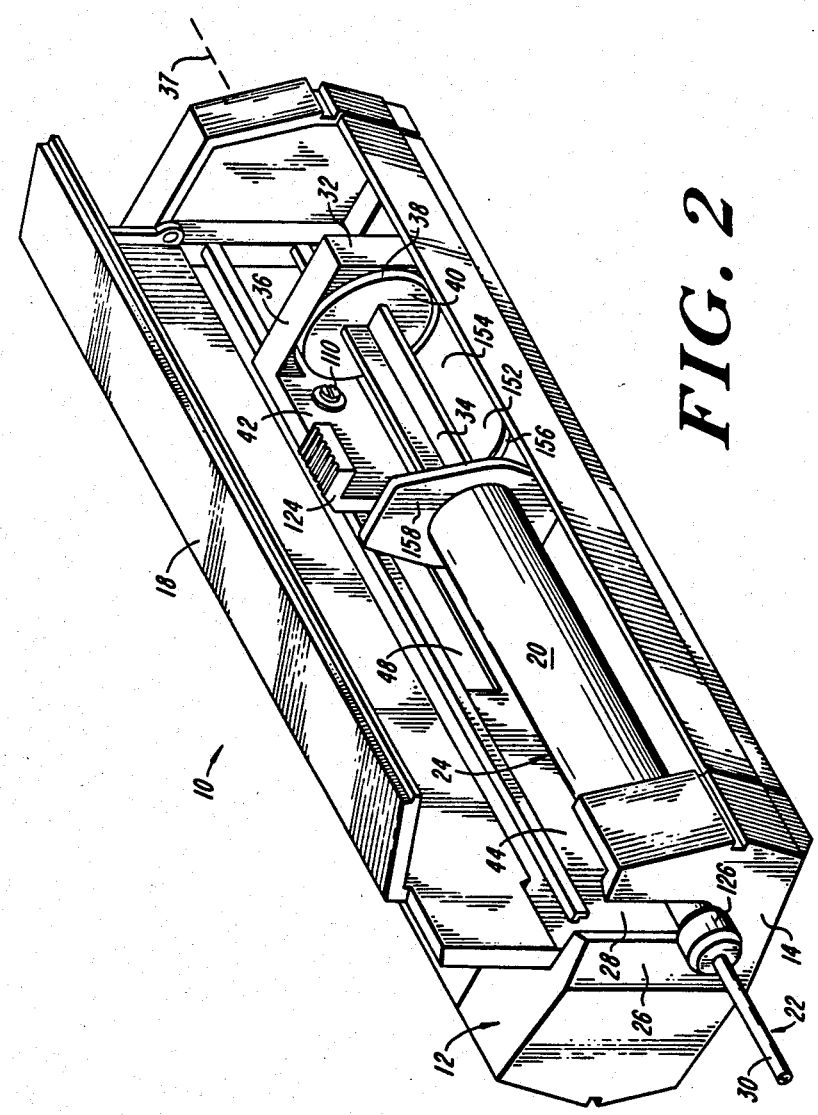
FIG. 2 is a view like that of FIG. 1 with a hinged door of the device open to show the syringe compartment of the device.

As shown in FIGS. 1 and 2, the infusion device 10 embodying the invention includes an elongate housing 12 having a base member 14 and a hinged door 18 that may be opened to insert a syringe 20 and tubing set 22 in a syringe compartment 24 of the device 10. The door 18 and the cover 16 are appropriately molded so that the door 18 can be snapped shut for operation of the device 10 after a syringe 20 is placed into it.

The housing 12 also includes a front, or toe, portion 26 that defines an open topped slot 28 when the door 18 is open. The slot 28 allows communication between the flexible tubing 30 of the tubing set 22 and the syringe 20 in the syringe compartment 24.

The syringe compartment 24 extends along the length of one side of the device 10. Located in the syringe compartment 24 is a movable plunger driver 32 for engagement and movement of the plunger 34 of a syringe 20 placed in the compartment 24. The plunger driver 32 has a generally planar vertical end portion 36 perpendicular to the axis 37 of the syringe compartment 24, including a saucer shaped shallow recess 38 in which the end 40 of a plunger 34 may be seated. Another portion of the plunger driver 32 is a vertical plate 42 that extends parallel to the compartment axis 37 along a dividing wall 44 separating the syringe compartment 24 from the drive assembly compartment 46. The dividing wall 44 includes a longitudinal slot 48 for connection between elements in the syringe 24 and drive assembly 46 compartments.

Figures 3, 4:
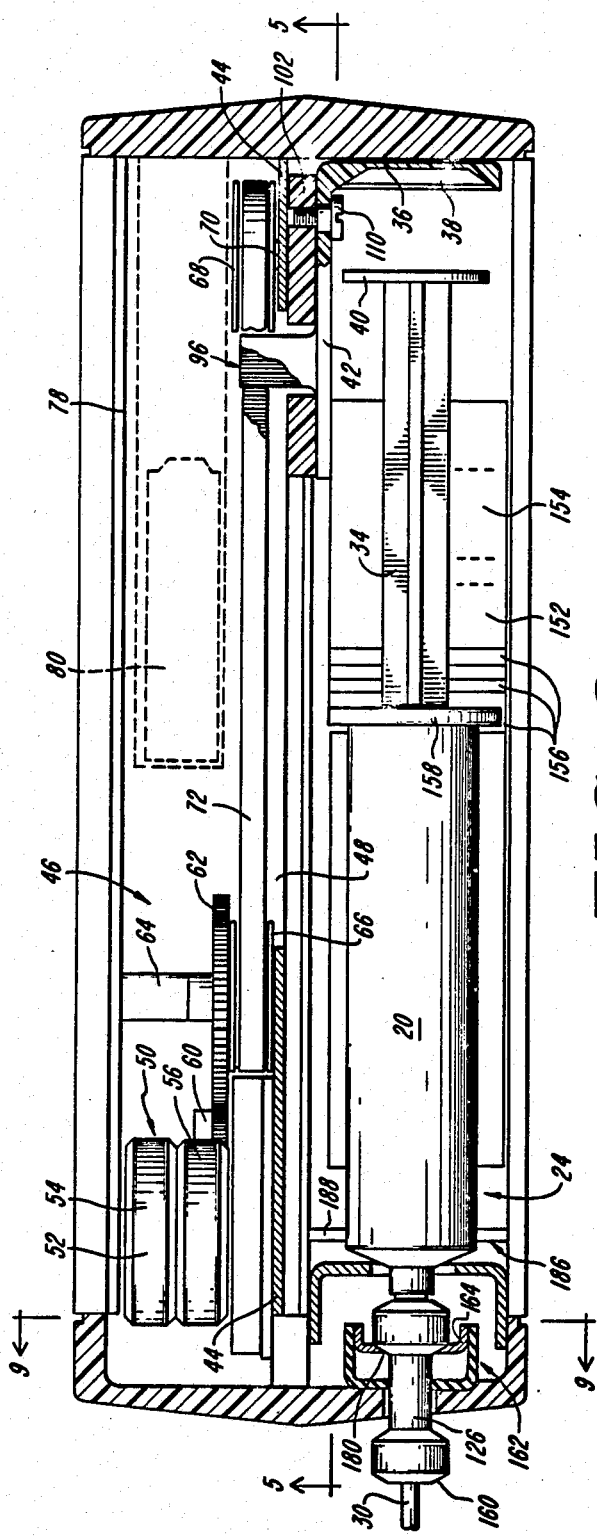
FIG. 3 is a plan view of the infusion device with the top cover removed in which one size syringe is located in the syringe compartment.
FIG. 4 is a partial plan view like FIG. 3 showing a different size syringe in the syringe compartment.
Figure 5:
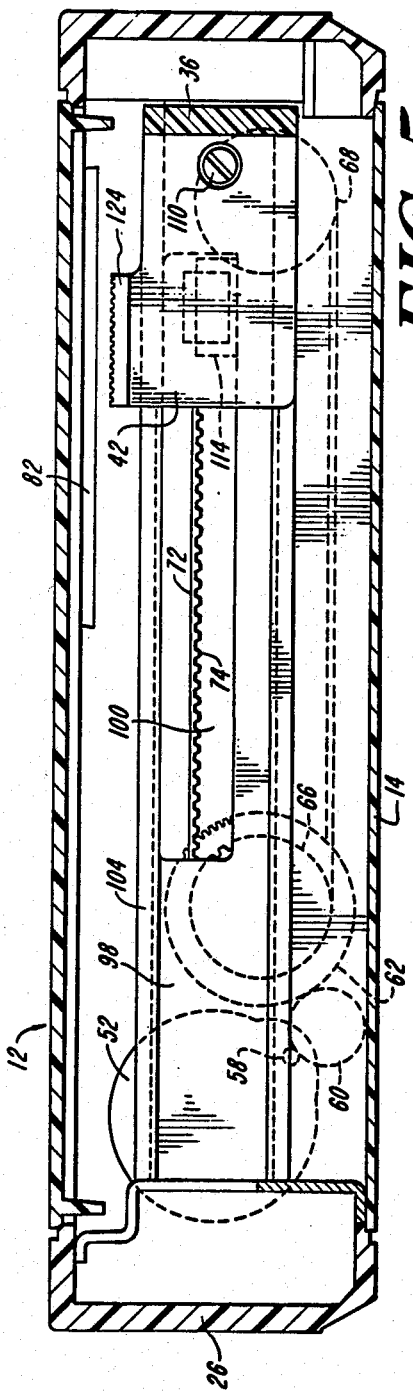
FIG. 5 is a sectional side view of the device along the line 5—5 of FIG. 3.

The drive assembly compartment 46 (see FIGS. 3 and 5) houses near the front portion 26 a stepper motor assembly 50 affixed to the wall 44 of the compartment 46. The stepper motor assembly 50 of the preferred embodiment includes a stepper motor and gear assembly unit 52 for stepping down the output of the shaft of the stepper motor 54. An example of such a stepper motor assembly 52 is the Airpax motor assembly sold under the model number K82237-P2 by North American Philips Control Corp. of Cheshire, Connecticut. The gear ratio of the gear assembly unit 56 of the stepper motor assembly 52 is about 60 to 1. The output shaft 58 of the stepper motor assembly 52 engages a gear external 60 to the assembly that drives a final large drive gear wheel 62 mounted for rotation on a shaft 64 affixed to a wall of the drive compartment 46, adding another 3 to 1 ratio to the total gear ratio between stepper motor 54 and final drive gear wheel 62. On the same shaft 64 for rotation, and fixed to the gear wheel 62, is a first drive pulley wheel 66 that accordingly rotates with the gear wheel 62. At the other, rear, end of the drive compartment 46 is a second, idler, pulley wheel 68 rotatably mounted on a shaft 70 fixed to the drive compartment 46. In the present embodiment the pulley wheels 66 and 68 are 1.0 inch diameter wheels, and have their axes spaced apart by 5.625 inches.

An endless drive belt 72 (see FIG. 6) is wrapped around the two pulley wheels 66,68 for translational movement in response to rotation of the first drive pulley 66, which, of course, rotates in response to the stepper motor 54. The belt 72 is made up of flexible material, and includes ridges 74 on the inside surface of the belt that are perpendicular to the direction of travel 76 of the belt 72, for positive engagement of the belt by other elements in the device.

Figure 14:
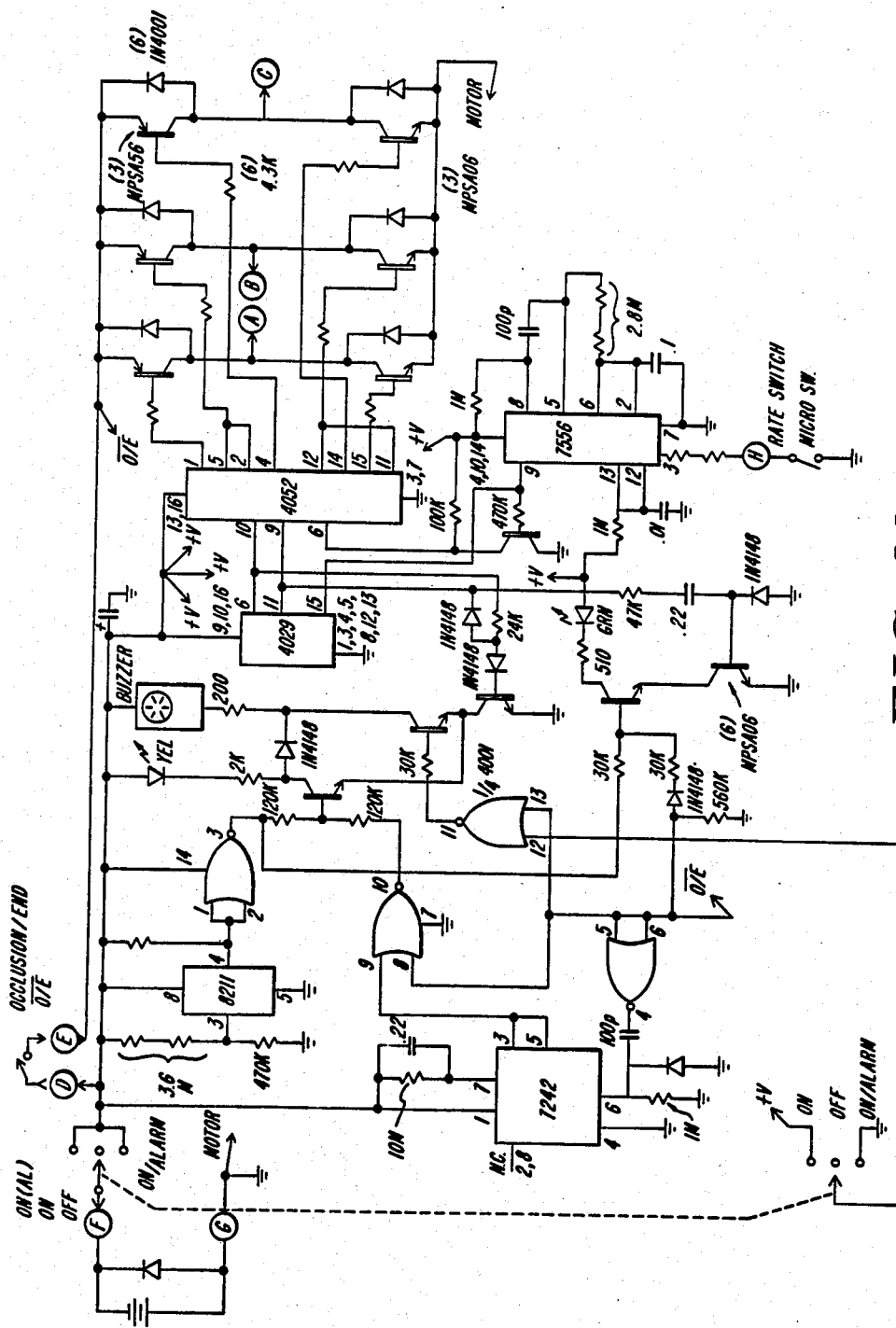
FIG. 14 is a schematic diagram of the control circuit for the device for bipolar operation.
Figure 15:
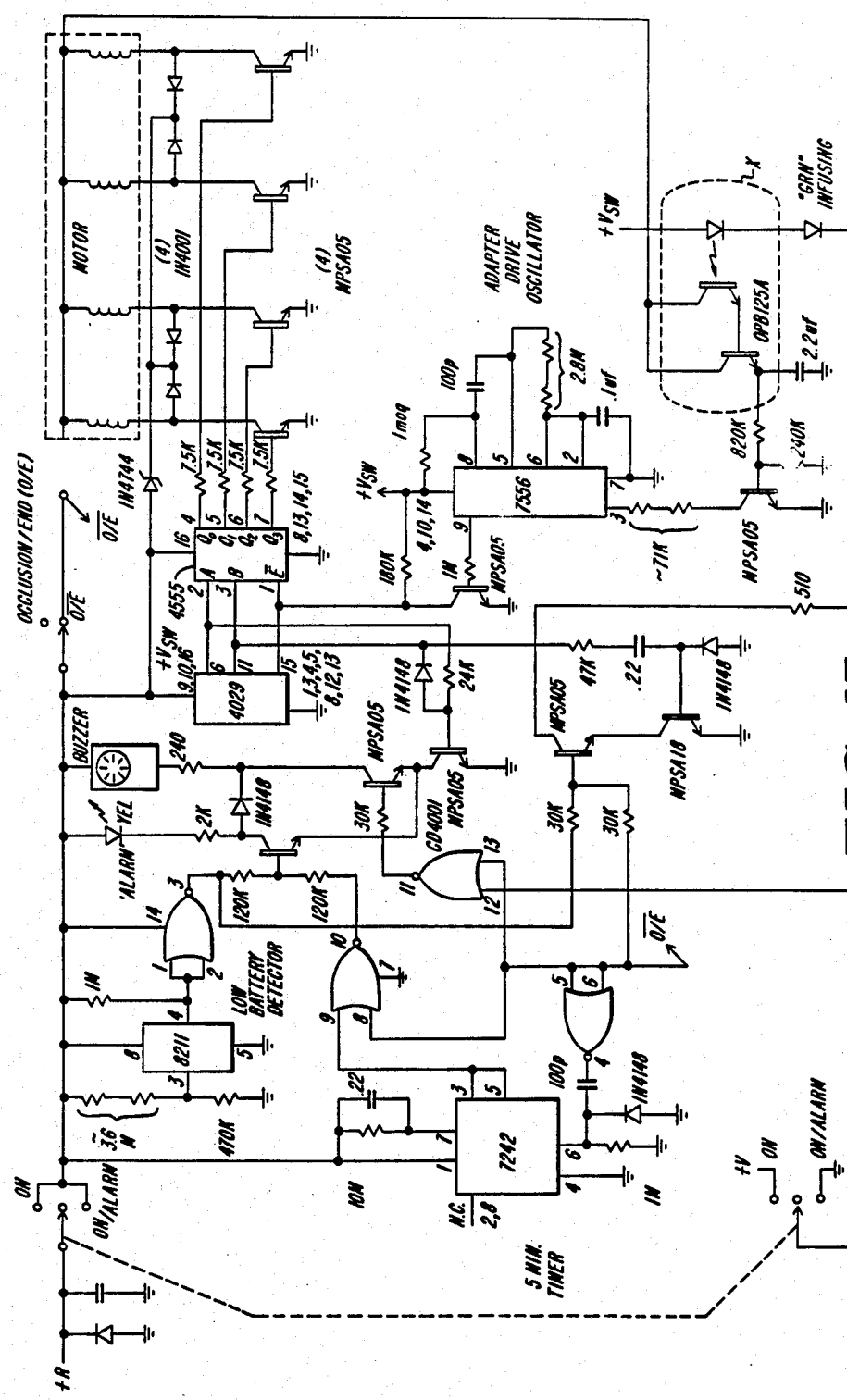
FIG. 15 is a schematic diagram for an alternate, unipolar, operation.

The drive compartment 46 also includes a battery compartment 78 for holding four batteries 80 to be used as a power source for the stepper motor 54 and an electronic control circuit (described below). Suitable electrical connections between the batteries 80, control circuit and the stepper motor 54 are made in ways known to those skilled in the art. A printed circuit board 82 houses the circuit for controlling operation of the stepper motor 54 in response to switches and sensors and is located in the drive compartment 46. FIGS. 14 and 15 illustrate schematic diagrams that set forth two exemplary control circuits of the present embodiment. In the disclosed embodiment, the stepper motor is adapted to drive the belt in a unidirection manner. The control circuit of FIG. 15 provides a unipolar pulsed mode of operation, and the control circuit of FIG. 14 provides a bipolar mode of operation. With the motor in the present embodiment, either control circuit may be used. In each case, the control circuit and motor configuration are pulse configurations in which substantially no power is drawn between pulses, permitting relatively long operation on a set of batteries. In other configurations, different control and motor arrangements may be used.

A ratchet assembly 84 (see FIG. 13), is affixed to the stepper motor 54 to permit operation with minimum power consumption. In the present configuration, a ratchet wheel 56 of rigid material (such as ABS) with outwardly directed teeth 58 is affixed to the rotor of the motor 54. A ring 90 of flexible material, such as polyethylene, with an inwardly directed, resilient pawl 92 is mounted on the housing of the motor 54 so that the pawl 92 can engage the ratchet wheel 86 at discrete locations corresponding to the discrete steps that the rotor of a stepper motor 54 takes during operation of the motor. The ratchet ring 90 includes a set screw 94 so that the pawl 92 can be oriented at a location corresponding to the stepper motor rotor's discrete locations. With this ratchet assembly, incremental unidirectional motion of the motor drive shaft may be established, without requiring power drawn by the motor between pulses in order to maintain an established position.

The control circuit of the circuit board 82 provides a controlled operation of the stepper motor 54. Depending on the rate of speed of the plunger 34 desired, the stepper motor 54 is pulsed with power to rotate it a discrete step, and then power to the motor from the battery source is effectively disconnected. For example, the motor 54 may be pulsed for 10 milliseconds in a timed operation of the motor, and then power may be disconnected for 500 milliseconds between timed operations. This disconnection of the power to the stepper motor 54 conserves electrical energy. The ratchet assembly ensures that the position of the stepper motor is maintained between pulses of power.

Figure 6:
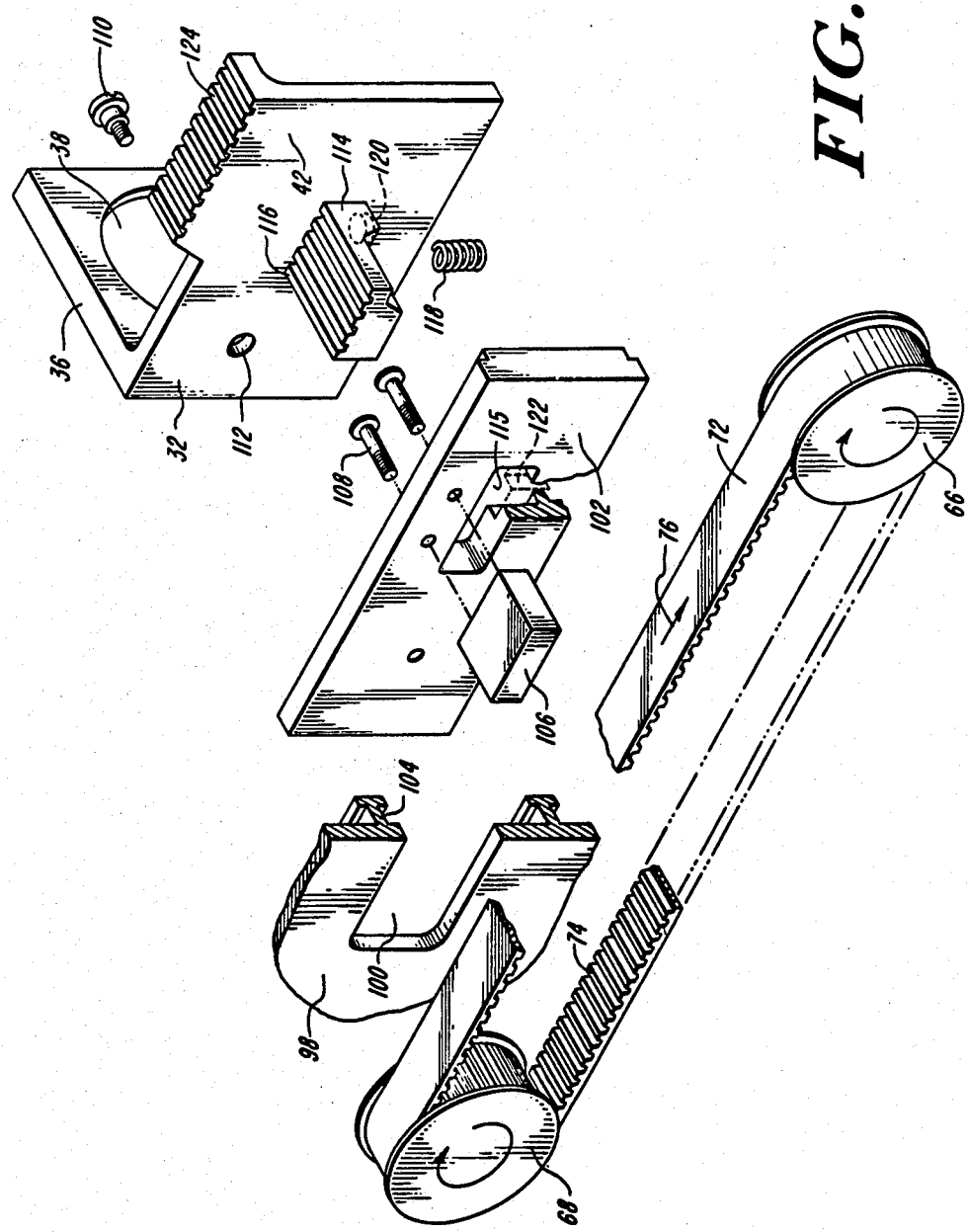
FIG. 6 is an exploded view of the slide and the plunger driver of the infusion device.

The drive belt 72 is selectively connected to the plunger driver 32 by a form of clutch assembly 96 (see FIG. 6). The assembly 96 includes an elongate channel member 98 affixed to the dividing wall 44 of the housing 12. The channel member 98 includes an elongate opening 100 corresponding to the opening 48 in the dividing wall 44 for communication between the two compartments 24,26.

A vertical slider 102 is captured between the edges 104 of the channel member 98 for longitudinal movement along the channel member 98. A horizontal base pad 106 is secured to the slider 102 (in the preferred embodiment, by screws 108) and projects from the slider 102, through the slot 48, into the drive compartment 46, above and adjacent to the outer surface of the drive belt 72.

The plunger driver 32 is connected to the slider 102 by a screw 110 passing horizontally through a hole 112 in the plunger drive plate 42 and secured to the slider 102. The plunger driver 32 is movable, hence pivotable, about the central axis of the screw 110. A clutch pad 114 extends horizontally from the plunger driver plate 42, through an opening 115 in the slider 102, into the drive compartment 46, beneath the drive belt 72. The clutch pad 114 has located on its upper surface (beneath the belt) a set of parallel ridges 116 corresponding to the parallel ridges 74 of the belt 72 for effective engagement therewith.

Figure 7:
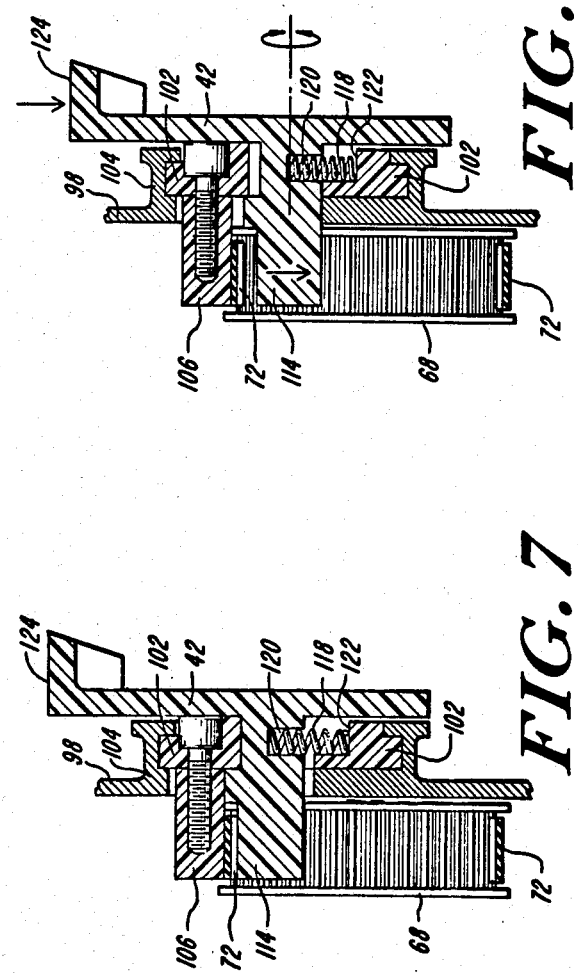

A coil spring 118 is captured between a recess 120 in the bottom of the clutch pad 114 and a recess 122 in the slider 102. The spring biases 118 the clutch pad 114 of the plunger driver 32 upwardly against the belt 72 so that the belt 72 is captured between the clutch pad 114 and the base pad 106 for firm engagement of the plunger driver 32 with the belt 72 (see FIG. 7).

Figure 8:
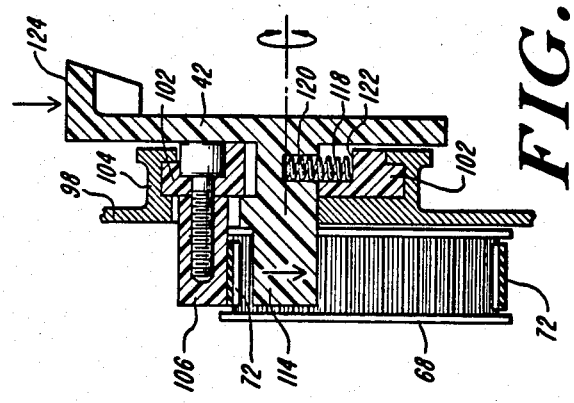
FIGS. 7 and 8 are views showing the relationship of the slide, plunger driver, and drive belt for engagement of the drive belt.

The plunger driver 32 includes a horizontal upper lever tab 124 positioned above the spring 118 so that downward pressure on the tab 124 pivots the plunger driver plate 42 (and clutch pad 114) downwardly against the bias of the spring 118, and moves the clutch pad 114 from engagement with the belt 72 (see FIG. 8). The plunger driver 32 and slider 102 can then be moved longitudinally, as a unit, independently of the belt 72. This is done to position the plunger driver 32 in the syringe compartment 24 before operation of the infusion device 10.

In the preferred embodiment the infusion device 10 is used in cooperation with a tubing set 22 having a connector 126 like that shown in FIGS. 11 and 12 coupled to an elongated flexible tube. The connector 126 is a tubular plastic element 128 having a central bore 130 with an axis 132 into which is embedded at one end the elongated flexible tubing 30 for intravenous use. The tubing 30 has a central passageway 134 for the passage of fluid from the syringe 20 through the tubing 30. It is coupled to the connector member 126 so that the central bore 130 of the connector 126 communicates with the central passageway 134 of the tubing 30. In the preferred embodiment, the tubing is polyvinyl chloride 85-90 durometer with a microbore interior diameter (less than 0.020") and a thick wall.

As shown in FIGS. 11 and 12 the end of the connector 126 opposite the tubing 30 includes a syringe-connect portion 136 for mounting the connector member 126 on the outlet end portion 138 of a syringe 20. The connector member 126 defines a recess 140 within which the syringe-connect portion 136 is located. The syringe-connect portion 136 includes a substantially cylindrical projection 142 having an inner central bore 144 communicating with the connector bore 130. The connect portion's inner bore 144 is adapted to receive the nozzle 146 of a syringe end portion 138 in a tightly fitting engagement. The outer surface 148 of the cylindrical projection 142 is tapered outwardly and rearwardly in a luer taper to engage, if necessary, a corresponding surface 150 on the syringe 30. It is not necessary to threadedly secure the connector 126 to the syringe 20 because, as will be seen later, the positioning of the connector 126 in the infusion device 10 prevents its disengagement from the syringe 20.

With the connector 126 mounted on a syringe 20, the syringe 20 may be inserted into the syringe compartment 24 of the infusion device 10. The syringe compartment 24 includes a syringe support plate 152 having a concave upper surface 154 corresponding generally to the cylindrical surface of the syringes resting thereon. The support plate 152 includes a number of parallel grooves 156 for seating the flanges 158 of syringes 20 of different sizes. The grooves 156 are wide enough to permit some longitudinal movement of the syringes 20, particularly to allow enough movement to affect a force sensor assembly, to be described below. The grooves 156 are marked to indicate the size of the syringe 20 to which they correspond.

The position of the connector 126 in the infusion device 10 is determined by the size of the syringe 20. For smaller syringes (e.g., those of 10 cc and 20 cc capacity), the entire connector 126 will be inside the infusion device, and only the flexible tubing 30 will extend through the slot 28 at the front of the device 10 (see FIG. 4). For larger and longer syringes (e.g., those of 30 cc capacity), a portion of the connector 126 will extend through the slot 28 (see FIG. 3). Accordingly, the starting point for the plunger driver 32 will be approximately the same regardless of the size of the syringe 20. Furthermore, detection of the position of the connector 126 in the infusion device 10 will determine whether small or large syringes are in the device. In some cases, smaller syringes may be emptied at higher speeds than larger syringes, with the position of the connector being used to control the speed of the drive motor assembly 52, as will be seen below.

If a smaller syringe 20 is used, the proximal, annular surface 160 of the connector 126 (the surface closest to the tubing 30) will abut a force sensor assembly 162 located just inside the front, or toe, portion 26 of the device housing 12. The force sensor assembly 162 comprises a metal U-shaped plate 164 with a surface 160 engaged by the actuating annular surface of the connector 126.

The sensor plate 164 is pivotally secured to the housing 12 to pivot about an axis 168 perpendicular to the axis 37 of the syringe compartment 24. The sensor plate 164 includes a surface 170 extending to meet a contact plate 172, against which it is pivotally biased by a spring 174 on a screw 176 passing through a hole 178 in the sensor plate 164. As long as fluid is proceeding without occlusion out of the syringe 20 under action of the plunger 34, the sensor plate 164 does not move away from contact with the contact plate 172 against the biasing force of the spring 174. If there is an occlusion, or if the end of the plunger travel has been reached, the force that results will be transmitted to the syringe 20 and connector 126 and then by the connector actuating surface 160 to the sensor plate 64. The force of the spring 164 is calibrated so that this larger force will cause the sensor plate 164 to pivot and break contact between the sensor plate 164 and contact plate 172, sending an appropriate signal to the control circuit 82 to actuate an alarm, or shut off the motor.

The connector 126 is arranged so that it has two parallel surfaces 160,180, spaced apart along the axis of the connector 126, for actuating the force sensor 162, depending on where the connector 126 is located in relation to the infusion device 10. If a small syringe is used in the infusion device 10 (see FIG. 4), the connector 126 will be located entirely inside the infusion device 10, and the front actuating annular surface 160 of the connector 126 will be in abutting engagement with the sensor plate 164. If a large syringe is used (see FIG. 3), the midsection 182 of the connector 126 will occupy the slot 28, and the rear actuating annular surface 180, parallel to the front actuating surface 160, will engage the force sensor plate 164. The connector 126 thus forms a "dumbbell" shape, with outwardly extending annular portions 184 at either end to form the actuating surfaces 160,180.

The infusion device 10 is arranged to provide different rates of plunger travel depending on size of the syringe 20 in the syringe compartment 24. The position of the connector 126 relative to the front of the infusion device 10 is the basis in the embodiment for determining which rate of speed should be used. The infusion device 10 in the embodiment includes a microswitch assembly 186, including an arm or plate 188 intruding into the toe portion 26 of the syringe compartment 24 where the connector member 126 is located during operation of the device 10. The microswitch arm 188 will occupy one position when the intermediate midsection, or interface, portion 182 of the connector 126 is contacted by it, and another position when an outwardly extending annular portion 184 of the connector is contacted. The different positions are translated by the control circuitry into different speeds of the operation of the driver stepper motor 54. The speed is doubled, for example, by allowing only 250 milliseconds between pulsed operations of the stepper motor 54, rather than 500 milliseconds, as described above. A second microswitch assembly, not shown, may be included to sense whether a syringe 20 is in the compartment at all.

An alternative embodiment is to have an optical sensor sensing a surface of the connector 126. The connector, in those circumstances, would have different surface textures or different optically reflecting properties, at axially spaced apart locations on the connector, so that the different characteristics sensed would indicate which size syringe is in the infusion device. The unipolar circuit of FIG. 15 includes position sensor (denoted x) which may be positioned near the toe of the syringe compartment to provide this optical sensing operation. In yet other embodiments, a sensor may be used which detects the electrical conductivity of certain regions of the connector 126, with the conductivity of those regions being different so that the position of connector 126 along the reference axis may be determined.

In operation, the tubing set 22, which includes the flexible tubing 30 to carry the fluid from the infusion device 10, is coupled to a syringe 20 by mounting the syringe-connect portion 136 on the syringe outlet end portion 138. Because the syringe-connect portion 136 is recessed in the connector 126 (the outer edge 192 of the syringe-connect portion 136 is substantially at, or inward of, a plane (represented by the dashed line 194 in FIG. 12) defined by the end face 196 of the connector 126) the tubing 30 may be coupled to a syringe 20 with a minimum risk that the syringe-connect portion will be contacted by non-sterile surfaces, particularly, for example, the hands of personnel making the connections.

The syringe 20 is then placed in the syringe compartment 24, at a position corresponding to its size. The grooves 156 in the syringe support plate 152 may be used to locate the syringe. The connector 126 is also a guide. For smaller syringes it is placed entirely in the device housing 12; for larger ones, the connector is inserted in the slot 28. An indication of where the connector 126 is to be placed is given by the position of the plunger driver 32. It occupies almost the same starting position for all size syringes, requiring that the connector 126 be inside for small syringes and partially outside for large syringes.

The door 18 to the syringe compartment 24 may then be closed. A switch, not shown, may then be turned on to begin operation of the device 10. Upon actuation (see the circuit diagram of FIG. 14), the stepper motor 54 will be operated by the control means 82 of the device 10 to turn on for approximately 10 milliseconds, and advance a step. When it advances, the drive belt 72 does too (at about a 200 to 1 gear ratio), and so does the plunger driver 32. Then the power to the stepper motor 54 is disconnected by the control circuit 82, to conserve electrical energy. The ratchet assembly 84 assures that the advance of the stepper motor 54 is maintained during this period of shut-down of the motor, and that the motor shaft is in the correct position for the next advance.

If the control circuit 82 detects a smaller syringe in the housing 12, because of a signal from the microswitch assembly 186, it will re-energize the stepper motor 54 after a period of 250 milliseconds. This corresponds to a plunger driver speed that will empty a 10 cc or a 20 cc syringe in about a half-hour. If the control circuit 82 is informed by the microswitch 186 that a larger syringe is in place, the periods of shut-down will be longer (e.g. 500 milliseconds), and the plunger driver speed will be slower. By way of illustration, a 30 cc syringe would be emptied in about an hour.

If an occlusion occurs, or when the plunger reaches the end of its travel, the control circuit 82 will react to a signal from the force sensor assembly 162 to energize an alarm, such as a light or buzzer, and, if desired, shut off the motor.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In an infusion device and syringe positioned therein, said infusion device including means for driving the plunger of said syringe along a reference axis toward a fluid dispensing outlet port thereof, wherein said infusion device includes a support member for supporting said syringe said support member including at least one support surface, the improvement comprising:

a tube assembly coupled to said fluid dispensing outlet port of said syringe including:
A. an elongated tube defining a central bore therethrough, and
B. a rigid connector member affixed to said tube and defining a linear central bore extending therethrough, said bore defining a continuous passageway extending from an input port of said connector member, and said connector member including means for coupling said input port to said outlet port of said syringe, wherein said connector member includes at least two support portions spaced apart along the axis of said connector member central bore and an interface portion connecting said support portions, and wherein the outer surfaces of said support portions are substantially identical in shape, said shape being adapted to interfit with said one support surface of said support member, whereby either of said support portions may be supported by said one support surface of said support member.

2. A tube assembly according to claim 1 wherein said outer surfaces of said support portions are surfaces of revolution.

3. A tube assembly according to claim 1 wherein said infusion device further includes a sensor for sensing force applied thereto in the direction of said reference axis, and wherein said connector member includes at least two actuating means for selective interfering engagement with said sensor.

4. A tube assembly according to claim 3 wherein said actuating means includes at least two actuating surfaces for abutting engagement with said sensor.

5. A tube assembly according to claim 4 wherein said actuating surfaces are spaced apart along the axis of said connector member central bore.

6. A tube assembly according to claim 5 wherein said actuating surfaces are annular surfaces, each of said annular surfaces being defined by an associated one of said support portions.

7. A tube assembly according to claim 5 wherein said actuating surfaces are substantially parallel.

8. A tube assembly according to claim 1, wherein said device further includes a sensor for sensing the position along said reference axis of said outlet port of said syringe, wherein said connector member includes surface regions adapted for sensing by said sensor, each of said regions being representative of an associated one of said support portions being supported by said support member.

9. A tube assembly according to claim 8 wherein said sensor is an optical sensor and said regions are characterized by differing optical reflectivity.

10. A tube assembly according to claim 8 wherein said sensor is a mechanically actuated switch and said regions are characterized by different physical geometry.

11. A tube assembly according to claim 8 wherein said sensor is a conductivity sensor and said regions are characterized by different electrical conductivity.

12. A tube assembly according to claim 1 wherein said input port coupling means is inset within said connector member.

* * * * *